(12) United States Patent
Brown et al.

(10) Patent No.: US 8,491,486 B2
(45) Date of Patent: Jul. 23, 2013

(54) ASSESSING A SUBJECT'S CIRCULATORY SYSTEM

(75) Inventors: Jeevanjot Brown, Berkshire (GB); Vincent Crabtree, Leicestershire (GB)

(73) Assignee: Dialog Devices Limited, Loughborough Leicestershire (GB)

( * ) Notice: Subject to any disclaimer, the term of this patent is extended or adjusted under 35 U.S.C. 154(b) by 671 days.

(21) Appl. No.: 12/590,930

(22) Filed: Nov. 17, 2009

(65) Prior Publication Data
US 2010/0125214 A1 May 20, 2010

(30) Foreign Application Priority Data
Nov. 17, 2008 (GB) .................................. 0820982.7

(51) Int. Cl.
*A61B 5/02* (2006.01)
(52) U.S. Cl.
USPC ............................ 600/504; 600/506; 600/507
(58) Field of Classification Search
USPC .................................................. 600/481–506
See application file for complete search history.

(56) References Cited

U.S. PATENT DOCUMENTS

| | | | |
|---|---|---|---|
| 5,054,488 A | 10/1991 | Muz | 128/633 |
| 5,246,003 A | 9/1993 | DeLonzor | 128/633 |
| 5,645,440 A | 7/1997 | Tobler et al. | 439/160 |
| 5,665,477 A | 9/1997 | Meathrel et al. | 428/500 |
| 5,678,544 A | 10/1997 | DeLonzor et al. | 128/633 |
| 5,830,136 A | 11/1998 | DeLonzor et al. | 600/323 |
| 5,934,925 A | 8/1999 | Tobler et al. | 439/325 |
| 5,991,648 A | 11/1999 | Levin | 600/344 |
| 6,236,037 B1 | 5/2001 | Asada et al. | 250/221 |
| 6,280,216 B1 | 8/2001 | Bernier et al. | 439/251 |
| 6,388,240 B2 | 5/2002 | Schulz et al. | 250/206 |
| 6,541,756 B2 | 4/2003 | Schulz et al. | 250/221 |
| 6,553,241 B2 | 4/2003 | Mannheimer et al. | 600/323 |
| 6,934,570 B2 | 8/2005 | Kiani et al. | 600/324 |
| 7,048,687 B1 | 5/2006 | Reuss et al. | 600/300 |

(Continued)

FOREIGN PATENT DOCUMENTS

| | | |
|---|---|---|
| DE | 197 07 442 A1 | 7/1997 |
| EP | 0 127 947 | 5/1984 |

(Continued)

OTHER PUBLICATIONS

Allen et al. "Development of neural network screening aid for diagnosing lower limb peripheral vascular disease from photoelectric plethysmography pulse waveforms." Phsyiological Measurement. 14. 1993. pp. 13-22.*

(Continued)

*Primary Examiner* — Patricia Mallari
*Assistant Examiner* — Tiffany Weston
(74) *Attorney, Agent, or Firm* — Harrington & Smith

(57) ABSTRACT

An apparatus including an input interface configured to provide signals from at least two sensors for at least two postures including: signals, dependent upon blood presence, from a first sensor when a subject is in a first posture; signals, dependent upon blood presence, from the first sensor when the subject is in a second posture; signals, dependent upon blood presence, from a second sensor when the subject is in the first posture; and signals, dependent upon blood presence, from the second sensor when the subject is in the second posture; and processing circuitry configured to determine and output a metric by combining, according to predefined calibration data the provided signals.

36 Claims, 6 Drawing Sheets

U.S. PATENT DOCUMENTS

| | | |
|---|---|---|
| 7,186,966 B2 | 3/2007 | Al-Ali .................. 250/214.1 |
| 2006/0073719 A1 | 4/2006 | Kiani ..................... 439/134 |
| 2007/0021660 A1 | 1/2007 | DeLonzor et al. ........... 600/344 |
| 2007/0123756 A1 | 5/2007 | Kitajima et al. ............ 600/300 |
| 2007/0213619 A1* | 9/2007 | Linder .................... 600/481 |
| 2007/0244377 A1 | 10/2007 | Cozad et al. .............. 600/323 |
| 2007/0270699 A1* | 11/2007 | Crabtree et al. ........... 600/500 |
| 2008/0081791 A1 | 4/2008 | Huang et al. .............. 514/44 |
| 2008/0188728 A1 | 8/2008 | Neumann et al. ........... 600/336 |

FOREIGN PATENT DOCUMENTS

| | | |
|---|---|---|
| EP | 1 671 581 A1 | 6/2006 |
| GB | 2 419 403 A1 | 10/2005 |
| JP | 2004-195070 | 7/2004 |
| WO | WO 01/41634 A2 | 6/2001 |
| WO | WO 03/031961 A2 | 4/2003 |
| WO | WO 03/057030 A1 | 7/2003 |
| WO | WO 2005/065533 A1 | 7/2005 |
| WO | WO 2006/086010 A2 | 8/2006 |
| WO | WO 2007/093804 * | 8/2007 |
| WO | WO 2007/093804 A2 | 8/2007 |
| WO | WO 2009/062189 A1 | 5/2009 |

OTHER PUBLICATIONS

Allen et al., "Development of a Neural Network Screening Aid for Diagnosing Lower Limb Peripheral Vascular Disease From Photoelectric Plethysmography Pulse Waveforms", Physiol Meas. 14. (1994), (pp. 13-22).

* cited by examiner

ASSESSING A SUBJECT'S CIRCULATORY SYSTEM

FIELD OF THE INVENTION

Embodiments of the present invention relate to assessing a subject's circulatory system.

BACKGROUND TO THE INVENTION

The response of a subject's circulation system to a subject's posture change may depend upon characteristics of the blood such as its viscosity, characteristics of the circulation system such as its resistance and how the autonomous nervous system responds to maintain homeostasis.

Blood perfusion at a periphery may, for example, be dependent upon one or a combination of the following factors:—
1. vascular disease such as for example Raynaud's disease
2. genetic problems such as for example scleroderma
3. an abnormal vaso-constriction or vaso-dilation response from the autonomous nervous system instigated by for example diabetic neuropathy or alcoholism
4. drug treatments such as for example Beta blockers
5. auto-immune diseases such as for example Lupus It will therefore be appreciated that there may be many reasons why a subject's circulatory system response to a postural change may be "abnormal". Different pathologies may have the same or different effects on circulation.

It would be desirable to provide an interim clinical indicator that characterizes a response of the circulation system to a series of postural changes and provides a clinician with information which in combination with other information and the clinician's skill and knowledge may be used to assess whether or not pathology may be present. The medical practitioner can then, using his own medical knowledge, conduct independent investigations before identifying any pathology.

BRIEF DESCRIPTION OF VARIOUS EMBODIMENTS OF THE INVENTION

According to various, but not necessarily all, embodiments of the invention there is provided an apparatus comprising:
an input interface configured to provide signals from at least two sensors for at least two postures including:
 signals, dependent upon blood presence, from a first sensor when a subject is in a first posture;
 signals, dependent upon blood presence, from the first sensor when the subject is in a second posture;
 signals, dependent upon blood presence, from a second sensor when the subject is in the first posture; and
 signals, dependent upon blood presence, from the second sensor when the subject is in the second posture; and
processing circuitry configured to determine and output a metric by combining, according to pre-defined calibration data the provided signals.

The signals, for each combination of sensor and posture, may comprises at least one logarithm of detected light intensity.

The signals, for each combination of sensor and posture, may include separately a time varying component of detected light intensity and a quasi static component of detected light intensity.

The signals, for each combination of sensor and posture, may include separately a logarithm of a time varying component of detected light intensity and a logarithm of a quasi static component of the detected light intensity.

The signals, for each combination of sensor and posture, may include a signal based upon a light intensity signal detected at an optical reflectance sensor and a signal based upon a light intensity signal detected at an optical transmission sensor.

The signals, for each combination of sensor and posture, may include a signal based upon a light intensity signal detected at a first wavelength but not at a second wavelength and a signal based upon a light intensity signal detected at least the second wavelength but not the first wavelength.

The calibration data may be used to assess divergence of the provided signals from an expected average of a statistical model of expected signals to produce the metric.

The calibration data may define a non-linear combination of the signals.

The calibration data may be predetermined using machine learning.

The apparatus may be configured to emulate an artificial neural network comprising a plurality of nodes each of which has associated weights for inputs to the node, wherein the calibration data provides said weights.

The apparatus may further comprise a memory storing multiple sets of calibration data comprising a set of calibration data for each of a plurality of predetermined standard sequences of different body postures.

At least one of the sensors may provide signals from optical reflection detectors.

A change from the first posture to the second posture may be expected to cause a local, as opposed to systemic, circulatory reaction A change from the first posture to the second posture may cause, for the subject, a relative vertical displacement with respect to the subject's heart of a subject's peripheral limb without relative vertical displacement with respect to the subject's heart of the subject's head. At least the first sensor may be on the limb.

A change from the first posture to the second posture may be expected to cause a systemic circulatory reaction.

A change from the first posture to the second posture may cause, for the subject, a relative vertical displacement with respect to the subject's heart of the subject's head.

At least the first sensor may be on the subject's head. This first sensor may provide signals from an optical transmission sensor.

The metric may record a divergence of the signals from an expected pattern of signals that characterize an expected response of a normalized circulation system to the predetermined sequence of first and second postures.

A system may comprising: the apparatus and at least a first sensor and a second sensor. The first sensor may be at a first location and the second sensor may be at a second, different, location. The first sensor may detect light at a first wavelength but not at a second wavelength and the second sensor may detect light at the second wavelength but not at the first wavelength. The first sensor may be a reflectance sensor and may be attached without clamping using an opaque adhesive collar that closely circumscribes the reflectance sensor. The first sensor and second sensor may be attached to a flexible substrate comprising interconnects that are connectable to the apparatus via an interface, wherein a portion of the flexible substrate, underlying one or more of the interconnects, has a manufactured structural weakness and wherein, in use, the portion of the flexible substrate having the structural weakness connects with the interface which retains the substrate against removal such that on attempted removal of the flexible substrate from the interface the manufactured structural weakness breaks the one or more interconnects. The interface may additionally detach a portion of the flexible substrate to reveal an indicator. The first sensor and second sensor may be attached to a flexible substrate for application to a subject and may be connectable to the processing circuitry via a first set of interconnects embedded in the flexible substrate, wherein an ordering of the interconnects embedded in the substrate is dependent upon whether the flexible substrate is for use on a right limb or a left limb and wherein the ordering of the interconnects embedded in the substrate, in use, is indicative to the processing circuitry of whether the flexible substrate is applied to a right limb of the subject or a left limb of the subject. The first sensor and second sensor may be attached to a first side of a flexible reversible substrate and may be connectable to the processing circuitry via a first set of interconnects on the first side of the flexible substrate and wherein a third sensor and a fourth sensor may be attached to a second side of the flexible substrate and may be connectable to the processing circuitry via a second set of interconnects on the second side of the flexible substrate, wherein an ordering of the first set of interconnects across the first side of the flexible interconnect, when the first side of the flexible substrate is upwards facing, is different to an ordering of the second set of interconnects across the first side of the flexible substrate when the second side of the flexible substrate is upwards facing thereby enabling the processing circuitry to determine which side of the reversible flexible substrate is operational. First signals detected by the first sensor may be processed to produce parallel signals that have different frequency components before combination at the processing circuitry and wherein second signals detected by the second sensor are processed to produce parallel signals that have different frequency components before combination by the processing circuitry.

According to various, but not necessarily all, embodiments of the invention there is provided an apparatus comprising: a system for assessing a subject's blood circulation a first detector configured to detect signals dependent upon blood presence when the subject is in a first posture and when the subject is in a second posture; at least one other detector configured to detect signals dependent upon blood presence when the subject is in the first posture and when the subject is in the second posture; and processing circuitry configured to determine a metric by combining the detected signals from the first and second detectors for the first and second postures according to calibration data.

According to various, but not necessarily all, embodiments of the invention there is provided a method comprising: attaching optical sensors to a subject; connecting the optical sensors to the apparatus; and moving the subject through a predetermined ordered sequence of different postures including the first and second postures. The optical sensors may be attached by attaching a disposable flexible substrate to the subject. The disposable flexible substrate may be attached to a limb and may comprise at least one optical reflectance sensor. The flexible substrate may be attached using adhesive only and without the use of a clamping force. The disposable flexible substrate may be attached to a subject's head and comprises at least one optical transmission sensor.

According to various, but not necessarily all, embodiments of the invention there is provided an apparatus comprising: a method comprising: processing light intensity signals received from optical sensors positioned on a subject when the subject is moved through a predetermined sequence of at least three different postures according to a kinematic protocol to provide input signals; combining the input signals to produce and output a metric that quantitatively defines a response of the subject's circulatory system to the predetermined sequence of at least three different postures of the kinematic protocol.

According to various, but not necessarily all, embodiments of the invention there is provided an apparatus comprising: a flexible substrate; a first optical sensor at a first location on the flexible substrate arranged in a reflectance configuration and a first adhesive collar closely circumscribing the first optical sensor, a second optical sensor at a second location on the flexible substrate; and a second adhesive collar closely circumscribing the second optical sensor, wherein the first adhesive collar is configured to position the first sensor adjacent a subject's body for physiological sensing and wherein the second adhesive collar is configured to position the second sensor adjacent the subject's body for physiological sensing.

According to various, but not necessarily all, embodiments of the invention there is provided an apparatus comprising: a flexible substrate comprising a manufactured structural weakness; at least a first sensor and a second sensor attached to the flexible substrate; interconnects connected to the first and second sensors; and an interface for connecting the interconnects to a cable, wherein the manufactured structural weakness underlies one or more of the interconnects adjacent the interface.

According to various, but not necessarily all, embodiments of the invention there is provided an apparatus comprising: a reversible flexible substrate having a first side and an opposing second side; a first sensor and a second sensor attached to the first side of the reversible flexible substrate; a first set of interconnects, on the first side of the reversible flexible substrate, connected to the first and second sensors in a first order; a third sensor and a fourth sensor attached to the first side of the reversible flexible substrate; a second set of interconnects, on the second side of the reversible flexible substrate, connected to the third and fourth sensors in a second order; wherein the first order of the first set of interconnects across the first side of the flexible interconnect, when the first side of the flexible substrate is upwards facing, is different to the second order of the second set of interconnects across the second side of the flexible substrate when the second side of the flexible substrate is upwards facing.

According to various, but not necessarily all, embodiments of the invention there is provided an apparatus comprising: a flexible substrate for application to a subject, the flexible substrate comprising at least a first sensor and a second sensor; a set of interconnects supported by the flexible substrate and connected to the sensors; an interface for connecting the interconnects to remote processing circuitry; wherein an ordering of the interconnects is dependent upon whether the flexible substrate is for use on a right limb or a left limb and wherein the ordering of the interconnects is indicative, when the apparatus is in use, to the processing circuitry of whether the flexible substrate is applied to a right limb of the subject or a left limb of the subject.

According to various, but not necessarily all, embodiments of the invention there is provided a collection of flexible substrates wherein each flexible substrate is ergonomically configured to be applied to a different body part of a subject, and comprises:
 at least a first sensor and a second sensor;
 a set of interconnects supported by the flexible substrate and connected to the sensors;
 an interface comprising a common fixed physical configuration of interface connectors for connecting the interconnects to remote processing circuitry;
wherein an ordering of the interconnects with respect to the common fixed physical configuration of interface connectors is dependent upon the body part to which a flexible substrate is to be applied and wherein the ordering of the interconnects with respect to the common fixed physical configuration of interface connectors is uniquely indicative, when the flexible substrate is in use, to the processing circuitry of the body part to which the flexible substrate is attached.

According to various, but not necessarily all, embodiments of the invention there is provided an apparatus comprising: an input interface configured to provide signals dependent upon blood presence at least two locations for at least two postures including signals dependent upon blood presence at a first location when a subject is in a first posture, signals dependent upon blood presence at the first location when the subject is in a second posture, signals dependent upon blood presence at a second location when the subject is in the first posture, and signals dependent upon blood presence at the second location when the subject is in the second posture; processing circuitry configured to determine and output a metric by combining, according to pre-defined calibration data the provided signals.

According to various, but not necessarily all, embodiments of the invention there are provided methods, systems, apparatuses and computer programs as claimed as the appended claims.

According to various, but not necessarily all, embodiments of the invention there is provided a system and method for assessing a subject's circulatory system using optical sensors and multiple postural changes.

This provides the advantage of low cost, rapid pain free assessment of subject physiology by assessment of disturbances to the circulatory system.

It should therefore be appreciated that the present invention does not diagnose a disease but provides an interim clinical indicator which is of a type that is not dissimilar to body temperature, blood pressure, heart rate etc.

BRIEF DESCRIPTION OF THE DRAWINGS

For a better understanding of various examples of embodiments of the present invention reference will now be made by way of example only to the accompanying drawings in which.

DETAILED DESCRIPTION OF VARIOUS EMBODIMENTS OF THE INVENTION

Figure 1:
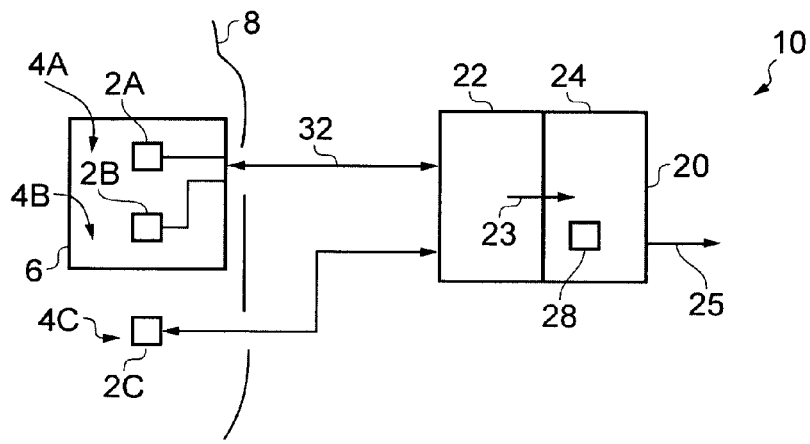
FIG. 1 schematically illustrates a system comprising: optical sensors and an apparatus.

Functional tests are used to provoke changes in the circulatory system of a subject. Functional test involves placing the subject into different postures and recording data at those postures. The exact number, type, order, frequency of postures used in a particular functional test protocol is predetermined and depends upon the subject's physiology and pathology under investigation.

A kinematic protocol (or test) is a sequence of three or more different postures. The sequence is typically carried out in a single continuous session. The sequence may be carried out as an uninterrupted sequence that does not have significant hiatus between postural changes.

The different postures adopted during a kinematic protocol may for example include at least three of: a reference posture, none, one or more 'local' (or 'limb') postures, none, one or more 'orthostatic' (or 'torso') postures, and none, one or more 'systemic' (or 'whole body') postures.

In a 'local' (or 'limb') posture, a limb has been moved through a gravitational field relative to a stationary body torso.

In a 'orthostatic' (or 'torso') posture, the body torso has been moved through a gravitational field relative to a stationary limb or limbs (e.g. legs).

In a 'systemic' (or 'whole body') posture, the whole body has been moved within a gravitational field but without relative movement between the body torso and limbs. This may be achieved by inclining a stationary subject.

The at least three different postures result in at least two different postural changes. The postural changes are changes of the whole or parts of the body relative to a gravitational field. The different postural changes therefore result in different 'impulses' to the subject's circulatory system.

It may be desirable to have a first type of impulse such as a 'local' (or 'limb') impulse by changing to a 'local' (or 'limb') posture or an 'orthostatic' (or 'torso') impulse by changing to an 'orthostatic' (or 'torso') posture or a 'systemic' (or 'whole body') impulse by changing to a 'systemic' (or 'whole body') position. It may be desirable to also have a different second type of impulse. Therefore if the first type of impulse was 'local' (or 'limb') the second type of impulse may be 'orthostatic' (or 'torso') or 'systemic' (or 'whole body') but not 'local' (or 'limb').

The following kinematic protocol can be used to assess a local response of a capillary bed i.e. vaso-dilation and vaso-contraction. A local postural change is followed by a systemic postural change.

First the local postural change is performed. An initial reference posture in which a subject is supine and an arm is level with the heart may be followed by a local posture in which the subject is supine and the arm is vertically displaced below the heart.

Then a systemic postural change is performed. An initial reference posture in which a subject is supine and an arm is level with the heart may be followed by a systemic posture in which the angle of incline of the body is changed without independent movement of the arm relative to the torso so that the head is vertically displaced below the heart.

A sensor may be located on an index finger of the arm. This sensor may be an optical transmission sensor which is sensitive to the arterial blood volume.

A sensor may be located on the forearm or the back of the hand. This sensor may be an optical reflection sensor which is sensitive to skin venous blood volume changes. The skin reflection sensor also permits normalizing of the digit transmission sensor caused by venous blood volume changes.

The outputs from the sensors have characteristics that produce different patterns as the kinematic protocol is performed. The patterns for a normal circulatory response share a common distinctive pattern. This distinctive pattern may be determined theoretically or empirically and then used to pattern match the outputs from the sensors for a subject during the same kinematic test. A metric may be output that indicates whether or the degree of pattern matching. A pattern match indicates a normal circulatory response for the given kinematic test. A pattern mismatch indicates an abnormal circulatory response that merits further investigation.

The following kinematic protocol can be used to assess arterial blood supply to the brain. An orthostatic (or body) postural change is followed by a systemic postural change.

First the orthostatic (or body) postural change is performed. The subject is initially in a supine reference position to record a baseline. The subject sits up or is sat up to an orthostatic (or body) posture, which would cause blood flow to the brain to initially reduce due to orthostatic pressure changes.

Then the systemic postural change is performed. The subject is returned to the supine reference position to record a baseline. The subject in the supine position is tilted so that the angle of incline of the body is changed so that the head is vertically displaced below the heart.

A sensor may be located on the subject's forehead. This sensor may be an optical reflection sensor which is sensitive to localized venous blood volume caused by pooling.

A sensor may be located across the nose. This sensor may be an optical transmission sensor which is sensitive to the arterial blood volume which is dependent upon the interior carotid artery via the ophthalmic and ethmoidal arteries.

A sensor may be located on an ear lobe. This sensor may be an optical transmission sensor which is sensitive to the arterial blood volume which is dependent on the external carotid artery via the temporal artery.

The sensors are preferably at approximately the same height to avoid orthostatic compensation.

The outputs from the sensors have characteristics that produce different patterns as the kinematic test is performed. The patterns for a normal circulatory response share a common distinctive pattern. This distinctive pattern may be determined theoretically or empirically and then used to pattern match the outputs from the sensors for a subject during the same kinematic test. A metric may be output that indicates whether or the degree of pattern matching. A pattern match indicates a normal circulatory response. A pattern mismatch indicates an abnormal circulatory response that merits further investigation such as a Magnetic Resonance Imaging (MRI) Scan if compromised blood supply to the brain is a possibility.

FIG. 1 schematically illustrates a system 10 comprising: optical sensors 2A, 2B, 2C and an apparatus 20.

The sensors 2A, 2B and 2C are positioned at respective locations 4A, 4B, 4C of a subject's body. In the example illustrated, the sensors 2A and 2B are attached to a substrate 6 and the substrate 6 is attached to the subject's body 8.

The sensors are non-invasive sensors typically photo sensors such as optical transmission sensors and/or optical reflection sensors. The sensors are for sensing physiological attributes such as, for example, changes in the volume of the body (plethysmography). An optical sensor comprises a light emitter and photo-detector. In a transmission sensor, in use, the photo-detector is positioned to receive light from the light emitter that has passed through the subject's body 8. In a reflection sensor, in use, the photo-detector is positioned to receive light from the light emitter that has been reflected by the subject's body 8.

It should be appreciated that the sensors 2A, 2B provide inputs to the apparatus 20 throughout the kinematic protocol i.e., for each posture of the subject.

Although only a single sensor is illustrated at each location, it should be appreciated that multiple sensors may be implemented at each location. For example, combinations of reflectance and transmission sensors may be provided in the same location. Also sensors that operate at different wavelengths of light may also be positioned at the same location. A sensor operating in near infrared of around 850 nm would be weakly affected by absorption in tissue but strongly affected by absorption by blood and could for example be used to monitor the reaction of a capillary bed during a kinematic test. Whereas a sensor operating around 650 nm would be strongly affected by absorption in tissue and could for example be used to monitor the reaction of skin tone during a kinematic test. The signal from the 850 nm sensor would have a much larger arterial component than the 650 nm sensor as it would penetrate deeper into tissue.

The sensors communicate with the apparatus 20 either using wireless methods (ZigBee, Bluetooth, UHF radio etc) or cables.

The apparatus 20 comprises an input interface 22 that pre-processes signals received from the sensors 2A, 2C and provides signal 23 to processing circuitry 24. The processing circuitry 23 is configured to determine and output a metric 25 by combining, according to pre-defined calibration data 28 the provided signals 23.

In the example illustrated, the provided signals 23 dependent upon blood presence at a first, second and third locations 4A, 4B, 4C when a subject is in the different postures of the kinematic protocol.

The interface 22 may also perform some signal processing before providing the signals 23 to the processing circuitry 24.

For example, the interface may separate an intensity signal from a sensor into two distinct signals having different frequency components. For example, it may produce an 'ac signal' that relates to the time varying intensity recorded at a sensor and a 'dc signal' that measures the quasi-static intensity recorded at the sensor.

As another example, the interface 22 may apply a non-linear function such as a logarithmic function to the signals 23 before they are provided to the processing circuitry 24.

The processing circuitry 24 may be implemented in any suitable manner. It may, for example, be a programmable computer or dedicated hardware. The interface 22 may be implemented in any suitable manner. It may, for example, comprise a programmable computer or dedicated hardware.

It should be appreciated that the interface 22 and processing circuitry may not be discrete physical components but may be functional modules implemented by common circuitry such as a processor executing different software modules.

The calibration data 28 is used to assess divergence of the provided signals 23 from an expected pattern of signals that characterize an expected response of a normalized circulation system to the kinematic protocol. The expected response may be an average of a statistical model of expected signals produced for example using machine learning.

The calibration data defines a non-linear combination of the signals. There will typically be different non-linear combinations of the signals 23 required for different kinematic tests as any pattern to be matched will vary with the location and type of sensors used and with the kinematic test performed. There will therefore be different calibration data 28 for each kinematic test.

Figure 2:
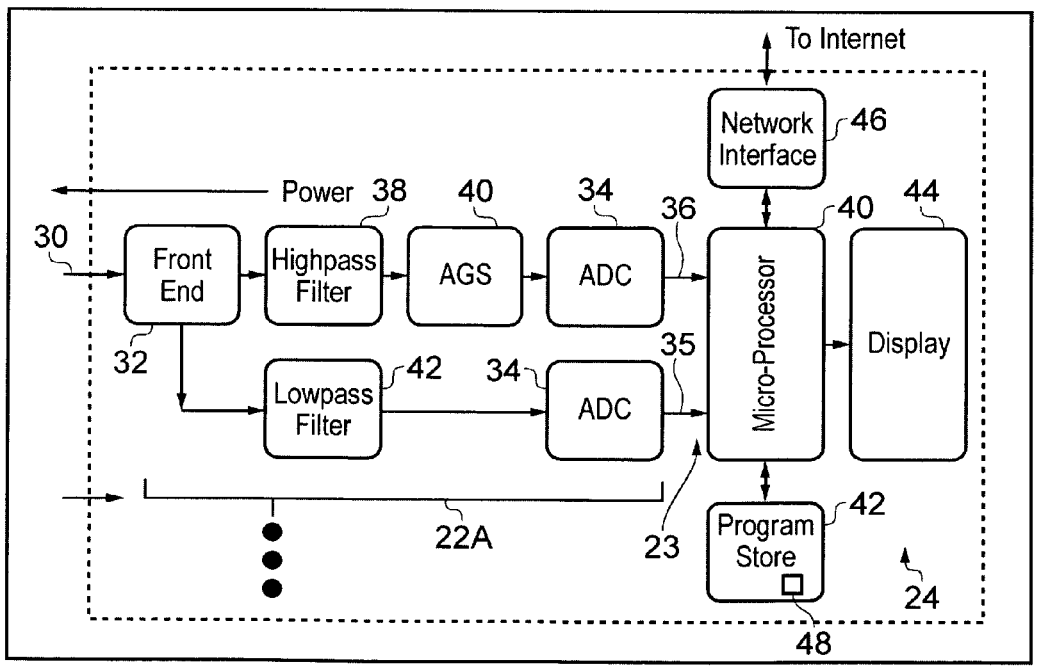
FIG. 2 illustrates the apparatus in more detail.

Referring to FIG. 2, the interface 22 comprises interface components 22A etc for one of the sensors 2A, however only the interface component 22A for the sensor 2A is illustrated. It should be appreciated that there will be an equivalent interface component.

The interface component 22A comprises analogue front end signal processing circuitry 32 for processing the intensity signal received from the sensor 2A and at least one Analogue to Digital converter 34.

There may be multiple front ends intended for simultaneous continuous monitoring of multiple sensors, or a single front end with an appropriate multiplexor switch. The front end circuitry may provide for constant control of the current provided to the sensors, trans-impedance amplification of the received signals 30, compensation for ambient light interference. This may be achieved using time division multiplexing (TDM), in which the periods where a light source is not illuminated, allows monitoring of ambient light interference. This may alternatively be achieved using frequency division implemented by employing a modulated light source and a frequency locking or demodulation system.

The front end circuitry 32 may initialize the sensors by configuring itself for a mid-scale value of the semi-static signal component by varying the LED intensity so the resultant signal would be mid way between a desired range, again for example unity. Any signal increases or decreases would be accommodated within the signal ranges, reducing the likelihood of signal saturation or diminishment.

In the example illustrated, the interface component 22A separates the received signal 30, after pre-processing, into two distinct signals 35, 36 having different frequency components.

It may produce an ac signal 36 by passing the received signal 32 through a high pass filter 38. The ac signal 36 relates to the time varying intensity recorded at a sensor. It may also produce a dc signal 35 by passing the received signal 32 through a low pass filter 42 that integrates, typically with a time constant of several seconds. The dc signal 35 relates to a quasi-static intensity recorded at the sensor. Filtering could be performed either in hardware using conventional linear time invariant filters or after digitization within a microprocessor using digital filters such as Finite impulse response designs. Digital filtering has the advantage of being able to change the filter parameters via software update if required.

The signal or signals (if high and low pass filtering has occurred) would then be fed to an analogue to digital converter (ADC) 35 before being provided to the processing circuitry 24. The ADC may be a discrete item or may be contained in a microprocessor.

A logarithmic function may be applied to signals before they are processed by the processing circuitry 24 to produce the metric 25. This logarithmic function may be applied in the analogue or digital domain. If applied in the digital domain, it may be applied by the interface 22 or the processing circuitry 24.

Optical absorption spectroscopy can be modeled using the Lambert-Beer Law, in which received optical intensity is proportional to an exponential function that has as its argument the product of a one dimensional optical path length and an absorption coefficient. Taking the natural logarithm of the received intensity produces a result that is linear in the optical path length. The optical path length may be assumed to vary depending on tissue blood volume, which is affected by posture and arterial dilation responses.

The processing circuitry in the illustrated example comprises a processor 40, a memory 42, a display 44 and a network interface 46. The processor 40 is configured to read from and write to the memory 42, to provide output commands to the display 44 and to communicate using the network interface 46.

The processor 40 would typically execute a program 48 from a memory 42 to calculate a metric 25 and then display the metric 25 on display 44.

The computer program may arrive at the apparatus via any suitable delivery mechanism. The delivery mechanism may be, for example, a computer-readable storage medium, a computer program product, a memory device, a record medium such as a CD-ROM or DVD, an article of manufacture that tangibly embodies the computer program. The delivery mechanism may be a signal configured to reliably transfer the computer program.

The exact form of the algorithm for a multi sensor, multi posture kinematic test is typically a summation of non-linear weighted input signals S 23. Some statistical manipulation may occur on the signals 23 before input to the algorithm. For example the median of a dc signal 35 may be calculated whereas a root mean squared value may be calculated for the ac signal 36.

The algorithm weights may be set using a-priori knowledge, or training using a teaching pattern and altering the weights according to the error.

If there are multiple postures i, multiple sensor sites j and multiple sensor wavelengths k at each sensor site, then the metric y could be defined as:

$$y = \sum_k \sum_j \sum_i c_{ijk} \log S_{ijk}$$

where $S_{ijk}$ is the input signal 23 for posture i, at site j for wavelength k.

Calculation of the weights c is possible using regression analysis. A multi posture kinematic test would be performed on a range of subjects who would also undergo independent clinical assessment. Then a least squares regression analysis of the recorded inputs against an idealized metric permits the algorithm weights to be defined.

Figure 3:
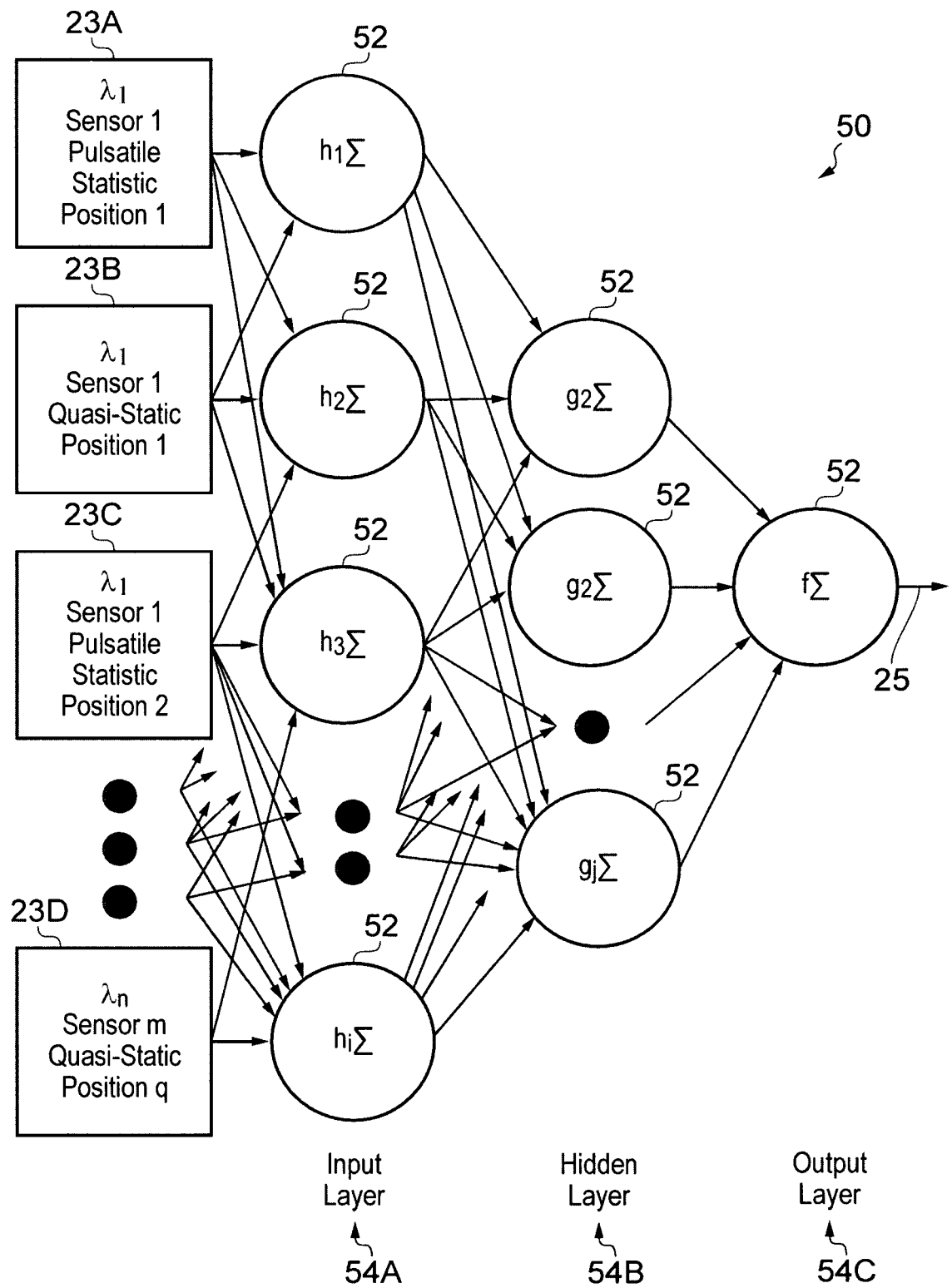
FIG. 3 schematically illustrates an artificial neural network for producing a metric.

Alternatively the metric could be defined as an arbitrary weighted summation of non-linear functions of the input signals $S_{ijk}$ using an artificial neural network 50 such as, for example, schematically illustrated in FIG. 3.

Artificial Neural Networks (ANN) are a class of non-linear weighting algorithms. The feed forward representation as illustrated in FIG. 3 consists of a directed acyclic graph of interconnected nodes 52 arranged in layers 54A, 54B, 54C.

The feed forward network 50 illustrated in FIG. 3 with three layers of neurons. Each input signal 23A, 23B, 23C, 23D is sent to every neuron 52 in an input layer 54A. Each neuron 52 in the input layer 54A forms its own weighted sum of its inputs 23A-D and provides the sum as an output. Each neuron 52 in the input layer 54A has its output connected to every neuron 52 in a hidden layer 54B. Each neuron 52 in the hidden layer 54B forms its own weighted sum of its inputs and provides the sum as an output. Each neuron 52 in the hidden layer 54B has its output connected to every neuron 52 in an output layer 54C. Each neuron 52 in the output layer 54C forms its own weighted sum of its inputs and multiplies the weighted sum by an activation function to produce the metric 25.

The metric 25 may be constrained to be a continuous value between 0 and 1 using a sigmoid function as the activation function, or between −1 and 1 using a hyperbolic tangent (Tan h) function as the activation function. If the metric is to be discrete, then a signum or step function could be used as the activation function.

In some implementations two layers 54 of neurons 52 may suffice.

The various weights applied in the weighted summations may be determined using supervised learning and back propagation. Alternatively optimum weights may be found using a genetic algorithm. The weights are comprised in the calibration data 28.

If there are i input nodes, j hidden nodes and only a single output node, the metric may be defined as $$f(x_i) = f \sum_j w_{g_1 \ldots j} \left( g_{v_j} \sum_i w_{h_1 \ldots i} \left( h_{v_i} \sum_i w_i x_i \right) \right)$$

Wherein are $h_{v_i}$, $g_{v_j}$, $x_i$ are:—

$$g_{v_j} = (g_1, g_2, \ldots, g_j), h_{v_i} = (h_1, h_2, \ldots, h_i),$$

$$x_i = (AC(\lambda_1 \ldots _n, P_1 \ldots _q)_{S_1}, DC(\lambda_1 \ldots _n, P_1 \ldots _q)_{S_1}, \ldots,$$
$$AC(\lambda_1 \ldots _n, P_1 \ldots _q)_{S_m}, DC(\lambda_1 \ldots _n, P_1 \ldots _q)_{S_m})$$

Note that $x_i$ represents a vector of statistic for the corresponding Sensor ($S_{1\ldots m}$) pulsatile component (AC) and quasi-static (DC) signal components for the different wavelengths ($\lambda_{1\ldots n}$) for each posture ($P_{1\ldots q}$).

The weights are defined using a training algorithm. Training, like in the simple algorithm above, requires known training data to be fed to the ANN, and the weights are modified using an error function or learning rule.

The network 50 would be trained by providing it with the input signal values for the postures obtained from a kinematic test and then matching using back propagation would be used to reduce an error between the output metric and an expected metric.

The steps for back propagation of ANN supervised learning may include:—
1. Present known training inputs to the ANN.
2. For each output neuron in the output layer, compare the ANN output metric to the expected metric for that known training sample and calculate the local error.
3. For each output neuron adjust the weights to lower the local error.
4. Assign different contributions for the local error to the neurons in the hidden layer, giving greater responsibility to neurons connected by stronger weights.
5. Repeat the steps 3 and 4 for the neurons in the hidden layer using each one's responsibility as its error.

It will be appreciated from the above that the metric is sensitive to the location of a sensor and the order and nature of the postures in a kinematic test.

To enable the correct order and nature of the postures to be performed for a kinematic test corresponding to the current calibration data 28, the apparatus 20 may give instructions either via a display 44 or by synthesizing a voice. The instructions would indicate when and how a posture of a subject should be changed.

There will be different sets of calibration data for different kinematic tests. A menu may be provided to select a particular test. The correct calibration data 28 would then be loaded for use by the apparatus 20 along with the instructions telling the operative how to perform the kinematic test.

It is also important that the sensors are located accurately and applied to a subject in a manner that does not arbitrarily interfere with the signals 23.

Figure 4A:
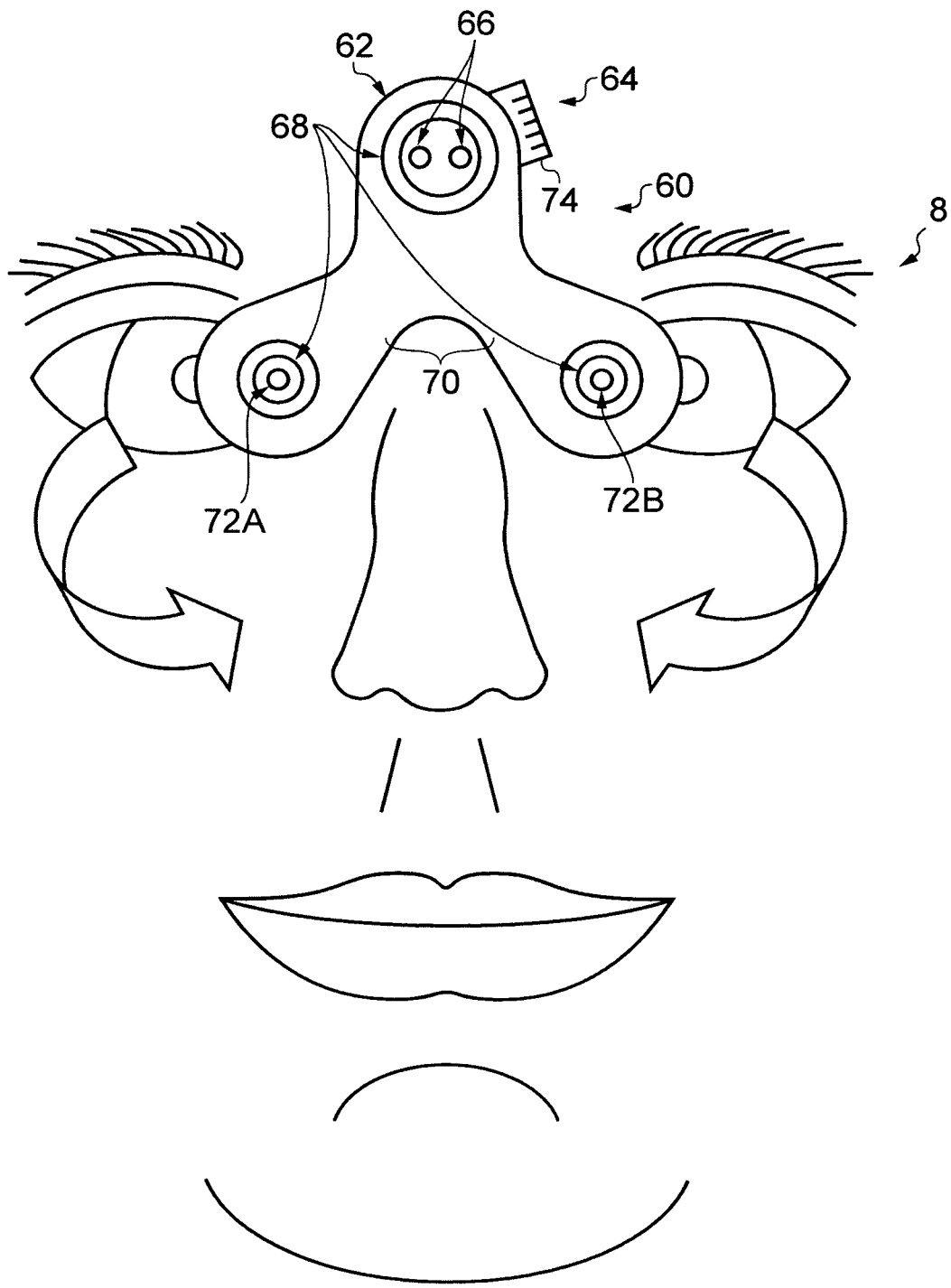
FIGS. 4A and 4B illustrate different implementations of a flexible substrate for sensors.
Figure 4B:
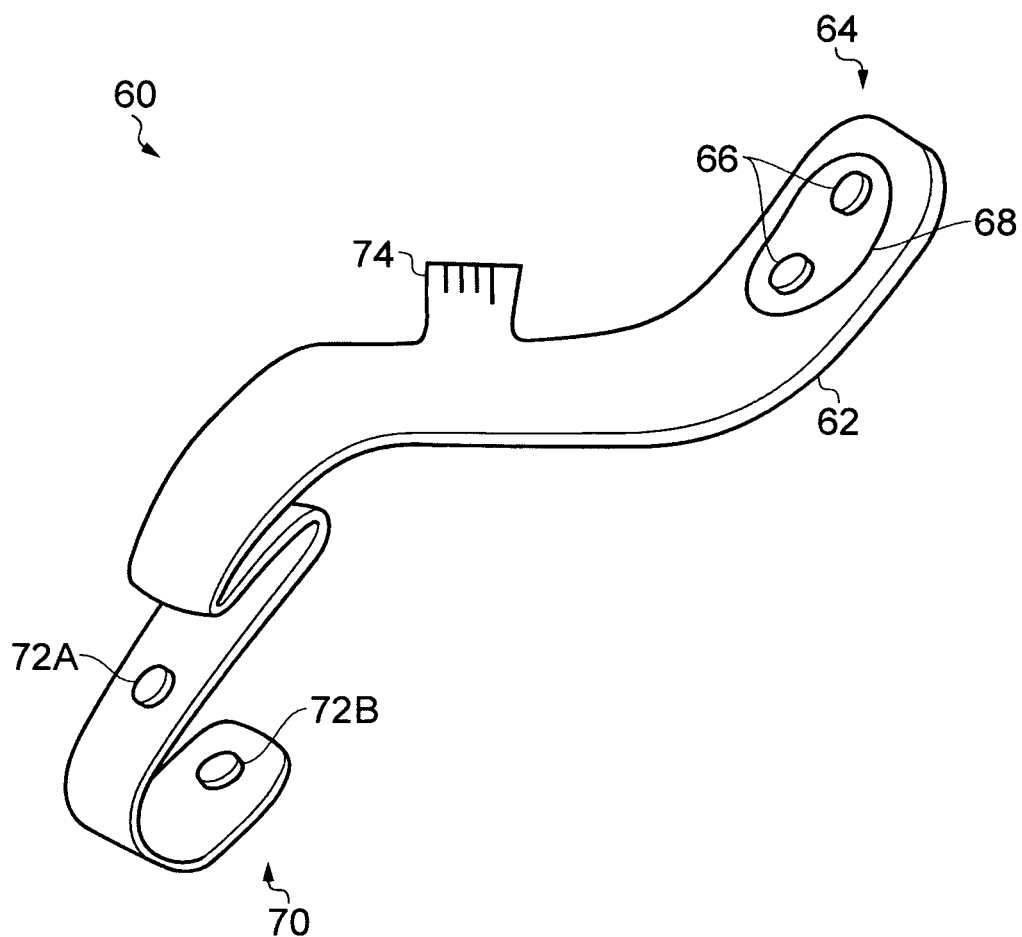

FIGS. 4A and 4B illustrate two different examples of apparatus 60 having flexible substrates 62 that are suitable for applying sensors to a subject 8.

The apparatus 60 illustrated comprises an ergonomically shaped flexible substrate 62.

At one end 64 of the flexible substrate 62 are located light emitter(s) and photo-detector(s) in an adjacent configuration in order to act as a reflection sensor 66.

An adhesive collar 68 that surrounds and closely circumscribes the reflectance sensor 66 is used to attach the end 64 of the flexible substrate 62 to the subject. The collar 68 is preferably substantially opaque at the wavelengths at which the photo-detector operates so that it acts to isolate the photo-detector from ambient light. The adhesive collar may be shaped like an annulus. The adhesive collar 68 may be formed from hydrogel.

A second portion 70 of the flexible substrate 62 is folded to act as a transmission sensor 72—a light emitter(s) 72A is applied to one side of a protuberance and a photo-detector(s) 72B is applied on the other side of the protuberance.

An adhesive collar 68 that surrounds and closely circumscribes the light emitter 72A and an adhesive collar 68 that surrounds and closely circumscribes the photo-detector 72B are used to attach the end 70 of the flexible substrate 62 to the subject. The adhesive collar circumscribes in the sense that it surrounds but it does not necessarily touch. The collars 68 are preferably substantially opaque at the wavelengths at which the photo-detector operates so that it acts to isolate the photo-detector from ambient light. The adhesive collar may be shaped like an annulus. The adhesive collar 68 may be formed from hydrogel.

The adhesive collars 68 adhere sensors in the correct strategic place and they avoid the use of a mechanical clip system, which would compress the arteries and veins in the bridge of the nose. This is especially important for reflectance sensors as they are sensitive to a vasodilatory response that would be masked by mechanical compression.

Conductive interconnects feed from an edge connector 74 (where the embedded contacts are exposed from within the flexible substrate and are inserted into a spring leaf type metal contact, one for each connector) to the ends 64, 70 of the flexible substrate 62, communicating with the light sources and photo-detectors.

Referring to FIG. 4A the flexible substrate 62 has a 'Y' or 'T' shape. The end 62 is located at the forehead of the subject. The end 70 is folded over the bridge of the nose to act as a transmission sensor.

The distance between the bridge of the nose and the reflection sensor on the head may be adjusted using a buckle (not shown), typically located between the eye brows which is only possible using a flexible substrate that will conform around the buckle. Alternatively the flexible substrate may be allowed to arch in order to accommodate excess length, as the hydrogel annulus adhesive should firmly affix the active components of the non-invasive optical sensors against the skin. The flexible substrate would typically be disposed of after use on a single subject to maintain hygiene and avoid subject cross contamination.

Referring to FIG. 4B the flexible substrate 62 has a 'Y' or 'T' shape. The end 62 is located over the extensor digitorum brevis muscle, located over the region of the third cuneiform, cuboid and metatarsal bones of the foot. The end 70 of the substrate 62 would wrap over the end of the locating toe (typically second toe). The transmission light emitter 72A is applied to the nail matrix and the transmission photo-sensor 72B is applied to the pad of the second toe, diametrically opposite the emitter 72A.

During application of the sensor to the subject, the flexible substrate is designed to conform to the subject's foot, naturally following the contours of the foot in order to locate over the second toe. The flexible substrate is shaped to follow the curvature of the foot, approximating a 'Z' shape which is easily achieved by stamping and laminating in conductive elements.

The advantages of the adhesive fixation method are that hydrogel adhesion locates the sensors in the correct strategic places on the foot rather than using mechanical clip systems or loops around the diameter of the toe. The arteries feeding the pulp of the toe pass alongside the side of the toe; therefore any method of securing the toe sensor which employs fastenings around the toe could compress the arteries and veins, spoiling the effects of the postural test. This is especially important if a vasodilatory response is to be observed as these mechanical effects would mask the homeostasis response.

In addition, adhesive pads may be located at strategic points along the flexible substrate to stabilize the substrate and reduce sensor movement and resultant motion artifact.

Figure 5A:
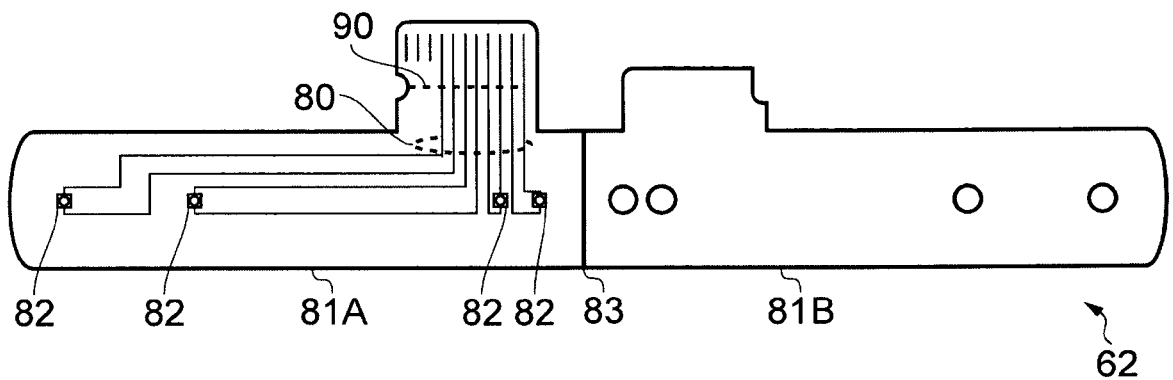
FIGS. 5A, 5B and 5C schematically illustrate safety features for flexible substrates.
Figure 5B:
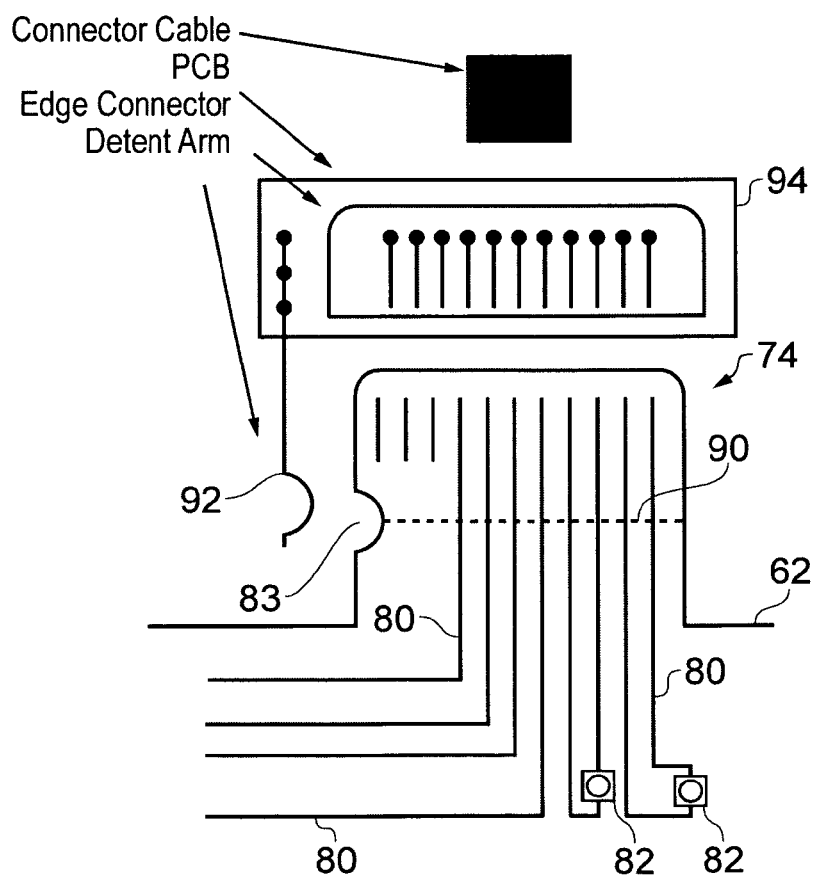

The flexible substrate 62 illustrated in FIG. 5B can with minor modification be made suitable for use with a hand. The reflectance sensor is located on the back of the hand and the transmission sensor is located on the index finger.

An alternative embodiment of this flexible substrate sensor would employ sensor elements on both sides of the substrate, permitting the substrate to be utilized on either foot.

Handedness Detection

A connecting cable connects with the edge conductor 74. The connecting cable has a series of contacts which are connected (perhaps semi-permanently) through the cable to particular parts of the front end circuitry 32. Consequently, the arrangement of the contacts at the interface of the connecting cable has, at least initially, a specific, predefined dedicated order. Thus a dedicated contact is always used to energize a first sensor and a dedicated contact is always used to receive.

Thus for example the following simplified table may illustrate a first correspondence between the contacts of the cable and those of the edge connector.

TABLE 1

| Cable Contact | | Connector Contact | |
| --- | --- | --- | --- |
| 1 | Output LED | 1 | Sensor 1 |
| 2 | Input LED | 2 | Sensor 1 |
| 3 | Output LED | 3 | Sensor 2 |
| 4 | Input LED | 4 | Sensor 2 |

The following simplified table may illustrate a second correspondence between the contacts of the cable and those of the edge connector.

TABLE 2

| Cable Contact | | Connector Contact | |
| --- | --- | --- | --- |
| 1 | Output LED | 1 | Sensor 1 |
| 2 | Input LED | 2 | Sensor 2 |
| 3 | Output LED | 3 | Sensor 2 |
| 4 | Input LED | 4 | Sensor 1 |

It is possible for the front end circuitry 32 to determine which of these configurations is used by applying an output LED control signal on only cable contact 1. If an input is received at the front end circuitry 32 on connector contact 2 then the first configuration is in use whereas if an input is received at the front end circuitry 32 on connector contact 4 then the second configuration is in use.

The different configurations may be used to identify different substrates 62.

Alternatively, the same substrate may be reversible with the first configuration used on one side and the second configuration used on the other side. This would enable the front end circuitry to determine the handedness of the substrate i.e. whether it is applied to a left or right foot. The front-end circuitry may then for example change how it provides signals to the substrate and how it interprets signals from the substrate.

It would also be possible to add redundant and/or degenerate contacts to create different configurations.

It is therefore possible to have a collection of flexible substrates where each substrate is ergonomically configured to be applied to a different body part of a subject. Each substrate may comprise the same (or different) sensors and will have a set of interconnects supported by the flexible substrate that connect to the sensors. Each substrate will also have an interface comprising a common fixed physical configuration of interface connectors (connector contacts) for connecting the interconnects to remote processing circuitry via the cable. An ordering of the interconnects with respect to the common fixed physical configuration of interface connectors is dependent upon the body part to which a flexible substrate is to be applied. The ordering of the interconnects with respect to the common fixed physical configuration of interface connectors is uniquely indicative, when the flexible substrate is in use, to the processing circuitry of the body part to which the flexible substrate is attached.

Safety Control

Figure 5C:
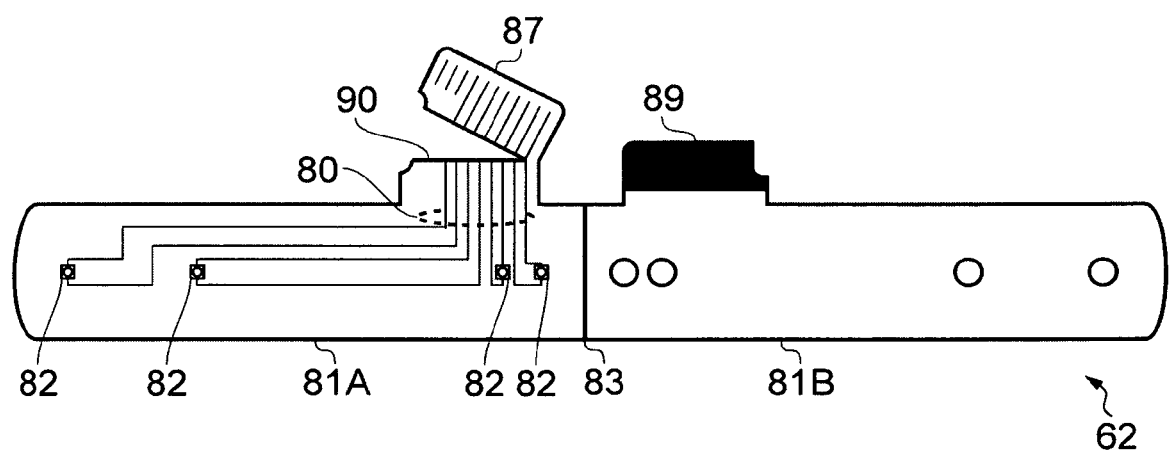

Referring to FIGS. 5A, 5B and 5C, the flexible substrate 62 may have a score or partial cut 90 (kiss-cut) through close to the designated edge connector 74. The width of the score may be across the whole of a tab supporting the edge connector 74 or more typically across 90% the width, leaving some of the substrate un-scored. The scoring produces a localized structural weakness controlled by the depth of the score, the cross section of the substrate and the tensile strength of the substrate material.

The interconnects 80 connecting the edge connector 74 to sensors may be formed from conductive ink, the thickness of the ink is tightly controlled, so the cross sectional area is less in the width of the score, but still sufficient to carry the appropriate current.

The design of the connecting cable's distal end female edge connector 94 includes a spring loaded retainer 92 which engages with a notch 83 on the side of the substrate male edge connector 74, or alternatively the cable edge connector includes a spring loaded detent pin which engages with a hole in the substrate close to the exposed edges of the connector tab. These features are designed into an edge connector shroud and are inaccessible by the user. The preferred method would use a small section of Printed Circuit Board (PCB) as a chassis, with the edge connector mounted and soldered to the PCB with through hole pins, where a piece of spring steel formed to act as the retaining lever is also soldered to the PCB. The cable shroud then serves to protect and form a substantial, rigid enclosure which can accept the force of the retainer and force of the operator.

When the kinematic test is complete, the operator removes the substrate 62 from the subject in the conventional way. The sensor is removed from the subject as normal, but for the substrate 62 to be removed from the cable edge connector, the substrate must be firmly grasped and pulled in order to overcome the spring loaded retainer 92 located in the edger connector shroud. At this moment the substrate section with the score will break, fracturing the interconnects 80. The score 90 runs transversely across some or all of the interconnects 80.

As the substrate is only partially scored, a section of the substrate will still remain intact, holding the tab to the remaining substrate. This prevents the substrate from breaking into two and the edge connector tab from getting stuck in the female edge connector.

To further facilitate this, the substrate is formed as a laminate of two layers 81A and 81B that are folded about join 83 and adhered together (FIG. 5A). Less or no adhesive glue is applied between the layers where the layer 81A has a score 90. In this embodiment, the score is made only in the laminate layer 81A supporting the interconnects. The portion of this laminate layer 81A demarcated by the score breaks away and may detach (FIG. 5C). The retainer is however now no longer in effect, and the retained portion may be easily removed from the female edge connector.

The other laminated layer 81B underlying the detachable portion 87 of the laminate layer 81A may be colored 89 e.g. red. When the portion 87 of the laminate layer 81A detaches severing the interconnects 90, the underlying colored layer 89 is exposed. This would indicate to the user that the substrate 62 has been used and should be disposed.

This method of fracturing the conductive ink conductors is far superior to the accidental, possibly intermittent, fractured conductor produced by material fatigue reuse, since the proposed method for producing the fractured electrical conductor is defined and reliable. Attempting to reuse a substrate with fractured conductors would be detected by the front end circuitry 32 when it performs the standard self tests when initializing for a kinematic test. For example, detecting insufficient power being consumed by the LEDs indicates fracture in the LED conductor lines.

For additional security, a programmable component such as a fusible link may also be incorporated as part of the conductive ink inside the sensor, which permits a sensor to be marked as 'used' by the system after the test. The fusible link can be effected by carefully controlling the screen printing process to deliver a conductive ink section with a known cross sectional area for a given maximum power dissipation. A short electrical pulse substantially exceeding this maximum power dissipation would controllably disrupt the fusible link, leaving it open circuit. The fusible link would be brought out to an additional edge connector conductor, or would be part of the existing tracking inside the sensor.

The blocks illustrated in the Figs may represent steps in a method and/or sections of code in the computer program. The illustration of a particular order to the blocks does not necessarily imply that there is a required or preferred order for the blocks and the order and arrangement of the block may be varied. Furthermore, it may be possible for some steps to be omitted.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:

1. An apparatus comprising:
   an input interface configured to provide signals from at least two sensors for at least two postures including:
   signals, dependent upon blood presence, from a first sensor when a subject is in a first posture;
   signals, dependent upon blood presence, from the first sensor when the subject is in a second posture;
   signals, dependent upon blood presence, from a second sensor when the subject is in the first posture; and
   signals, dependent upon blood presence from the second sensor when the subject is in the second posture;
   processing circuitry configured to determine and output a metric by combining, according to pre-defined calibration data the provided signals; and
   a memory storing multiple sets of calibration data comprising a set of calibration data for each of a plurality of predetermined standard sequences of different body postures; wherein the processing circuitry is configured to determine and output a metric for a particular predetermined standard sequence of different body postures by combining, according to calibration data for the particular predetermined standard sequence of different body postures, the provided signals.

2. An apparatus as claimed in claim 1, wherein the provided signals, for each combination of sensor and posture, comprises at least one logarithm of detected light intensity.

3. An apparatus as claimed in claim 1, wherein the signals, for each combination of sensor and posture, include a time varying component of detected light intensity and a separated quasi static component of detected light intensity.

4. An apparatus as claimed in claim 1, wherein the signals, for each combination of sensor and posture, include separately a logarithm of a time varying component of detected light intensity and a logarithm of a quasi static component of the detected light intensity.

5. An apparatus as claimed in claim 1, wherein the signals, for each combination of sensor and posture, include a signal based upon a light intensity signal detected at an optical reflectance sensor and a signal based upon a light intensity signal detected at an optical transmission sensor.

6. An apparatus as claimed in claim 1, wherein the signals, for each combination of sensor and posture, include a signal based upon a light intensity signal detected at a first wavelength but not at a second wavelength and a signal based upon a light intensity signal detected at, at least, the second wavelength but not the first wavelength.

7. An apparatus as claimed in claim 1, wherein the calibration data is used to assess divergence of the provided signals from an expected average of a statistical model of expected signals to produce the metric, wherein the provided signals comprise signals that have been statistically manipulated to be averaged signals.

8. An apparatus as claimed in claim 1, wherein the calibration data is predetermined using machine learning.

9. An apparatus as claimed in claim 1, configured to emulate an artificial neural network comprising a plurality of nodes each of which has associated weights for inputs to the node, wherein the calibration data provides said weights and wherein the artificial neural network receives as inputs the provided signals wherein the provided signals comprise signals that have been statistically manipulated to be averaged signals.

10. An apparatus as claimed in claim 1, wherein at least one of the sensors provide signals from optical reflection detectors.

11. An apparatus as claimed in claim 1, wherein at least the first sensor is configured to be placed on a limb of the subject.

12. An apparatus as claimed in claim 1, wherein at least the first sensor is configured to be placed on the subject's head.

13. An apparatus as claimed in claim 12, wherein the first sensor provides signals from an optical transmission sensor.

14. An apparatus as claimed in claim 1, wherein the pre-defined calibration data is used to assess a divergence of the provided signals from an expected pattern of signals that characterize an expected response of a normalized circulation system to the predetermined sequence of first, second and third postures.

15. An apparatus as claimed in claim 1, wherein the processing circuitry is configured to combine, according to pre-defined calibration data the provided signals, by using summation and weightings.

16. A system comprising:
at least a first sensor and a second sensor; and
an apparatus comprising:
an input interface configured to provide signals from at least the first sensor and the second sensor for at least two postures including:
signals, dependent upon blood presence, from the first sensor when a subject is in a first posture;
signals, dependent upon blood presence, from the first sensor when the subject is in a second posture;
signals, dependent upon blood presence, from the second sensor when the subject is in the first posture; and
signals, dependent upon blood presence from the second sensor when the subject is in the second posture;
processing circuitry configured to determine and output a metric by combining, according to pre-defined calibration data the provided signals; and
a mentor storing multiple sets of calibration data comprising a set of calibration data for each of a plurality of predetermined standard sequences of different body postures, wherein the processing circuitry is configured to determine and output a metric for a particular predetermined standard sequence of different body postures by combining, according to calibration data for the particular predetermined standard sequence of different body postures, the provided signals.

17. A system as claimed in claim 16, wherein the first sensor is at a first location and the second sensor is at a second, different, location.

18. A system as claimed in claim 16, wherein the first sensor detects light at a first wavelength but not at a second wavelength and the second sensor detects light at the second wavelength but not at the first wavelength.

19. A system as claimed in claim 16, wherein the first sensor is a reflectance sensor and is attached without clamping using an opaque adhesive collar that closely circumscribes the reflectance sensor.

20. A system as claimed in claim 16, wherein the first sensor and second sensor are attached to a flexible substrate comprising interconnects that are connectable to the apparatus via an interface, wherein a portion of the flexible substrate, underlying one or more of the interconnects, has a manufactured structural weakness and wherein, in use, the portion of the flexible substrate having the structural weakness connects with the interface which retains the substrate against removal such that on attempted removal of the flexible substrate from the interface the manufactured structural weakness breaks the one or more interconnects.

21. A system as claimed in claim 20, wherein the interface additionally detaches a portion of the flexible substrate to reveal an indicator.

22. A system as claimed in claim 16, wherein the first sensor and second sensor are attached to a flexible substrate for application to a subject and are connectable to the processing circuitry via a first set of interconnects embedded in the flexible substrate, wherein an ordering of the interconnects embedded in the substrate is dependent upon whether the flexible substrate is for use on a right limb or a left limb and wherein the ordering of the interconnects embedded in the substrate, in use, is indicative to the processing circuitry of whether the flexible substrate is applied to a right limb of the subject or a left limb of the subject.

23. A system as claimed in claim 16, wherein the first sensor and second sensor are attached to a first side of a flexible reversible substrate and are connectable to the processing circuitry via a first set of interconnects on the first side of the flexible substrate and
wherein a third sensor and a fourth sensor are attached to a second side of the flexible substrate and are connectable to the processing circuitry via a second set of interconnects on the second side of the flexible substrate,
wherein an ordering of the first set of interconnects across the first side of the flexible interconnect, when the first side of the flexible substrate is upwards facing, is different to an ordering of the second set of interconnects across the first side of the flexible substrate when the second side of the flexible substrate is upwards facing thereby enabling the processing circuitry to determine which side of the reversible flexible substrate is operational.

24. A system as claimed in claim 16, wherein first signals detected by the first sensor are processed to produce parallel signals that have different frequency components before combination at the processing circuitry and wherein second signals detected by the second sensor are processed to produce parallel signals that have different frequency, components before combination by the processing circuitry.

25. A method comprising:
attaching at least a first optical sensor and a second optical sensors to a subject; and
connecting the optical sensors to an apparatus comprising:
an input interface configured to provide signals from at least the first sensor and the second sensor for at least two postures including:
signals, dependent upon blood presence, from the first sensor when a subject is in a first posture;
signals, dependent upon blood presence, from the first sensor when the subject is in a second posture;
signals, dependent upon blood presence, from the second sensor when the subject is in the first posture;
signals, dependent upon blood presence from the second sensor when the subject is in the second posture; and
processing circuitry configured to determine and output a metric by combining, according to pre-defined calibration data the provided signals; and
a memory storing multiple sets of calibration data comprising a set of calibration data for each of a plurality of predetermined standard sequences of different body postures, wherein the processing circuitry is configured to determine and output a metric for a particular predetermined standard sequence of different body postures by combining, according to calibration data for the particular predetermined standard sequence of different body postures, the provided signals, and
moving the subject through a predetermined ordered sequence of different postures including the first and second postures.

26. A method as claimed in claim 25, wherein the optical sensors are attached by attaching a disposable flexible substrate to the subject.

27. A method as claimed in claim 26, wherein the disposable flexible substrate is attached to a limb and comprises at least one optical reflectance sensor.

28. A method as claimed in claim 27, wherein the flexible substrate is attached using adhesive only and without the use of a clamping force.

29. A method as claimed in claim 26, wherein the disposable flexible substrate is attached to a subject's head and comprises at least one optical transmission sensor.

30. A method as claimed in claim 26, wherein moving the subject through a predetermined ordered sequence of different postures comprises moving the subject between postures to cause a local, as opposed to systemic, circulatory reaction.

31. A method as claimed in claim 26, wherein moving the subject through a predetermined ordered sequence of different postures comprises moving the subject between postured to cause, for the subject, a relative vertical displacement with respect to the subject's heart of a subject's peripheral limb without relative vertical displacement with respect to the subject's heart of the subject's head.

32. A method as claimed in claim 26, wherein moving the subject through a predetermined ordered sequence of different postures comprises moving the subject between postured to cause a systemic circulatory reaction.

33. A method as claimed in claim 26, wherein moving the subject through a predetermined ordered sequence of different postures comprises moving the subject between postures to cause, for the subject, a relative vertical displacement, with respect to the subject's heart, of the subject's head.

34. A method as claimed in claim 26, moving the subject through a predetermined ordered sequence of different postures including the first, the second posture and a third posture.

35. An apparatus comprising:
an input interface configured to provide signals from at least two sensors for at least two postures including:
signals, dependent upon blood presence, from a first sensor when a subject is in a first posture;
signals, dependent upon blood presence, from the first sensor when the subject is in a second posture;
signals, dependent upon blood presence, from a second sensor when the subject is in the first posture; and
signals, dependent upon blood presence from the second sensor when the subject is in the second posture; and
processing circuitry configured to determine and output a metric by combining, according to pre-defined calibration data the provided signals,
wherein the processing circuitry is configured to perform pattern matching between patterns produced by the provided signals during a kinematic protocol involving at least a change between first, second and third postures and normal circulatory response patterns.

36. An apparatus as claimed in claim 35, wherein the weightings are determined by training.

* * * * *

UNITED STATES PATENT AND TRADEMARK OFFICE
CERTIFICATE OF CORRECTION

PATENT NO.        : 8,491,486 B2
APPLICATION NO.   : 12/590930
DATED             : July 23, 2013
INVENTOR(S)       : Jeevanjot Brown and Vincent Crabtree Page 1 of 1

It is certified that error appears in the above-identified patent and that said Letters Patent is hereby corrected as shown below:

In the Claims:

In Claim 16:
Column 17, line 28, "mentor" should be deleted and --memory-- should be inserted.

Signed and Sealed this
Seventeenth Day of September, 2013

Teresa Stanek Rea
*Deputy Director of the UnitedStates Patent and Trademark Office*